(12) United States Patent
Yan et al.

(10) Patent No.: US 7,799,950 B2
(45) Date of Patent: Sep. 21, 2010

(54) DIAMINE AND POLYAMIC ACID DERIVED THEREFROM FOR LIQUID CRYSTAL ORIENTATION APPLICATIONS

(75) Inventors: Chuan-Ter Yan, Kaohsiung (TW); Chih-Hsiung Huang, Kaohsiung (TW); Chao-Ching Huang, Kaohsiung (TW); Chin-Wang Kao, Kaohsiung Hsien (TW); Tin-Hun Hung, Kaohsiung (TW)

(73) Assignee: Daily Polymer Co., Ltd., Kaohsiung Hsien (TW)

( * ) Notice: Subject to any disclaimer, the term of this patent is extended or adjusted under 35 U.S.C. 154(b) by 248 days.

(21) Appl. No.: 11/797,993

(22) Filed: May 9, 2007

(65) Prior Publication Data

US 2008/0281112 A1 Nov. 13, 2008

(51) Int. Cl.
*C07C 211/54* (2006.01)
*C07C 233/42* (2006.01)
*C07C 233/64* (2006.01)
*C07C 237/28* (2006.01)
*C07C 229/52* (2006.01)
*C07C 69/76* (2006.01)

(52) U.S. Cl. ........................ 564/426; 564/155; 564/156; 564/157; 564/305; 564/427; 560/19; 560/102; 560/116; 560/117

(58) Field of Classification Search .................. None
See application file for complete search history.

(56) References Cited

U.S. PATENT DOCUMENTS

| | | |
|---|---|---|
| 5,276,132 A | 1/1994 | Nishikawa et al. |
| 5,698,135 A | 12/1997 | Nishikawa et al. |
| 5,783,656 A | 7/1998 | Kimura et al. |
| 6,111,059 A | 8/2000 | Nihira et al. |
| 6,746,730 B1 | 6/2004 | Tanioka et al. |

OTHER PUBLICATIONS

Database CAPLUS on STN, Acc. No. 1973:515453, ACHT et al., DE 2163056 (Jun. 20, 1973) (abstract).*
Database CAPLUS on STN, Acc. No. 1990:424839, Ramalingham et al., Polyimides: Mater., Chem. Charact., Proc. Int. Conf. Polyimides, 3rd (1989), Meeting Date 1988, p. 479-486.*

* cited by examiner

*Primary Examiner*—Brian J Davis
(74) *Attorney, Agent, or Firm*—Finnegan, Henderson, Farabow, Garrett & Dunner, L.L.P.

(57) ABSTRACT

A diamine includes a structure of formula (I),

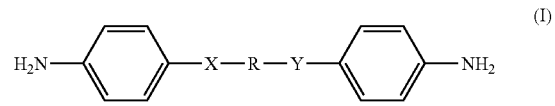

wherein X and Y are independently a divalence group selected from the group consisting of: —O—, —(C=O)—O—, —O—(C=O)—, —(C=O)—NH—, and —NH—(C=O)—; and R has a structure of formula (II):

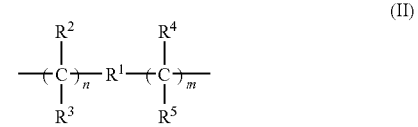

wherein $R^1$, $R^2$, $R^3$, $R^4$, $R^5$, m, and n are as defined in Claim 1. A polyamic acid is prepared by reacting a diamine reactant including the aforesaid diamine of formula (I) with a tetracarboxylic dianhydride reactant. A liquid crystal orienting film contains a polyimide converted from the aforesaid polyamic acid.

18 Claims, No Drawings

DIAMINE AND POLYAMIC ACID DERIVED THEREFROM FOR LIQUID CRYSTAL ORIENTATION APPLICATIONS

BACKGROUND OF THE INVENTION

1. Field of the Invention

This invention relates to a diamine and a polyamic acid derived from the diamine.

2. Description of the Related Art

Because of lightweight and low power consumption characteristics of a liquid crystal display apparatus, a miniature portable personal information device with a liquid crystal display panel has been widely developed. The arrangement of liquid crystal molecules in a liquid crystal layer of the liquid crystal display apparatus can be changed using an external electric field, thereby adjusting the transmitted amount of incident light. Based on different arrangements of the liquid crystal molecules, liquid crystal display apparatus presently in practical use can be classified into a twisted nematic (TN) liquid crystal display apparatus twisted by 90°, a super twisted nematic (STN) liquid crystal display apparatus twisted by 180° or more, or a liquid crystal display apparatus utilizing thin film transistors (TFT).

In general, TN liquid crystal display apparatus includes, from bottom to top, a first substrate, a first conductive film, a first orienting film, liquid crystal, a second orienting film, a second conductive film, and a second substrate. The first and second orienting films are used to allow liquid crystal molecules to tilt at a pre-tilt angle relative to the first and second substrates. There are two methods for producing the orienting film. The first method is vapor deposition of an inorganic material, such as silicon oxide, on the first and second substrates along an inclined direction so as to form the orienting films on the first and second substrates. The liquid molecules injected after formation of the orienting films can be arranged along the inclined direction. However, this method is not suitable for mass production in the industry. The second method includes forming an organic coating on each of the first and second substrates, and rubbing a surface of the coating along a predetermined direction using a fabric, such as cotton, nylon, or polyester, so as to form well-arranged grooves on the surface of the coating. The liquid crystal molecules injected after forming the grooves are arranged along the grooves. The second method is widely used because of well arrangement of the liquid crystal molecules and easy performance. In the second method, the organic coating can be formed from polyvinyl alcohol, polyoxyethylene, polyamide, or polyimide, in which polyimide is widely used due to high mechanical strength, heat resistance, and solvent resistance.

A conventional method for producing polyimide includes polymerizing a monoamine or a diamine and a tetracarboxylic dianhydride so as to form a polyamic acid, and heating the polyamic acid so as to form a polyimide. To obtain a proper pre-tilt angle (greater than 3°) and good orienting property without deteriorating the property of the polyimide, research has focused on the modification of diamine structure.

U.S. Pat. No. 6,111,059 granted to Nissan Chemical Industries Ltd. discloses a diaminobenzene derivative represented by the general formula (1)

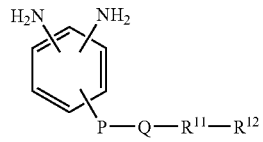

(1)

wherein P is a single bond or a bivalent organic group selected from —O—, —COO— and —CONH—, Q is a cyclic substituent selected from an aromatic ring, an aliphatic ring, a hetero ring and combinations thereof, $R^{11}$ is an aliphatic ring, and $R^{12}$ is a $C_{1-22}$ alkyl group having a linear chain. A polyimide is also disclosed in this patent, which is obtained by reacting a diamine containing at least 1 mol % of the diaminobenzene derivative with a tetracarboxylic acid to form a polyimide precursor followed by undergoing a ring-closing reaction. The polyimide has a repeating unit represented by the general formula (2)

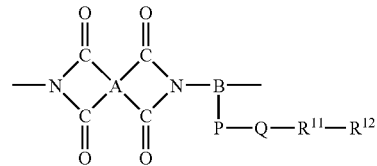

(2)

wherein A is a tetravalent organic group constituting a tetracarboxylic acid, B is a bivalent organic group constituting a diamine, and P, Q, $R^{11}$, and $R^{12}$ are as defined in the formula (1).

Japan Synthetic Rubber Co., Ltd. has proposed diamines and polyimides disclosed in, for example, U.S. Pat. Nos. 5,276,132, 5,698,135, and 5,783,656. U.S. Pat. No. 5,698,135 discloses a liquid crystal-aligning agent including at least one of polyamic acid (referred as "polymer I") and a polymer (referred as "polymer II") obtained by imidizing the polymer I. The polyamic acid is obtained by reacting a tetracarboxylic acid dianhydride with a diamine compound. The diamine compound is selected from the group consisting of:

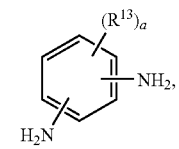

(3)

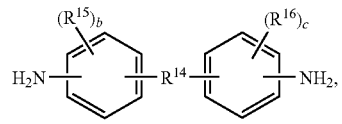

(4)

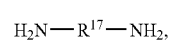

(5)

and combinations thereof. In formula (3), $R^{13}$ is a halogen atom, alkyl, or an alkoxyl group, and a is an integer of 0 to 4. In formula (4), $R^4$ is —$CH_2$—, —O—, —S—, formula (i), or formula (ii), $R^{15}$ and $R^{16}$ are independently a halogen atom or an alkyl group, and b and c are each independently an integer of 0 to 4.

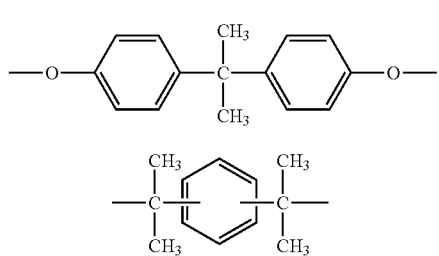

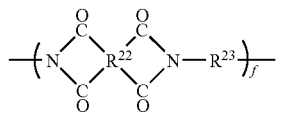

In formula (5), $R^{17}$ is a divalent organic group having a steroidal skeleton. Examples of formula (5) include formulas (6) and (7).

-continued wherein $R^{18}$, $R^{20}$, and $R^{22}$ are independently a tetravalent organic radical derived from tetracarboxylic acids; $R^{19}$, $R^{21}$, and $R^{23}$ are independently a divalent organic radical derived from a diamine compound; and d, e, and f are independently a positive integer. Examples of the diamine compound include formulas (11) to (15).

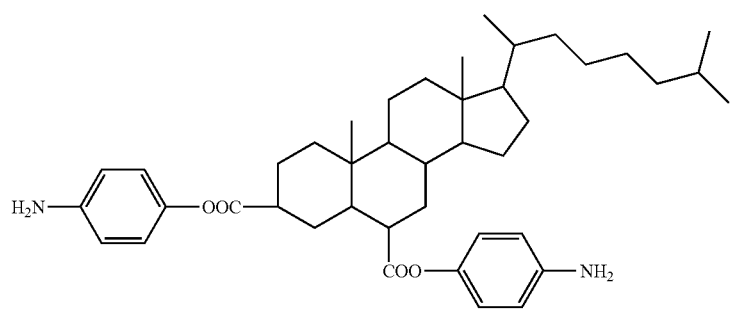

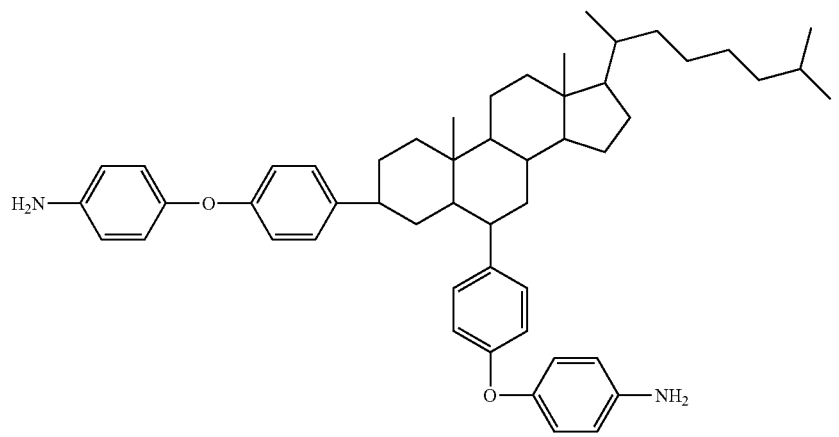

U.S. Pat. No. 6,746,730 granted to Chisso Corporation discloses a varnish composition which includes a polyamic acid B represented by formula (8), a polyamic acid A represented by formula (9), and a soluble polyimide represented by formula (10),

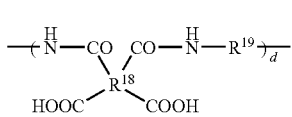

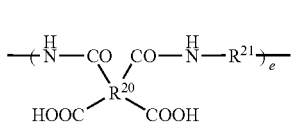

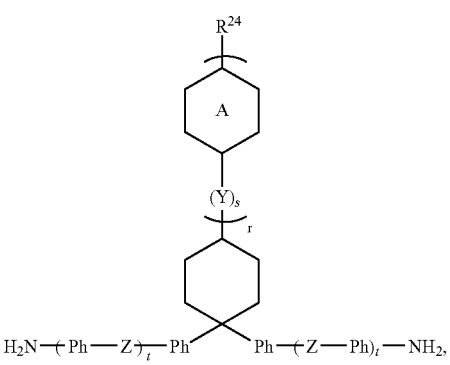

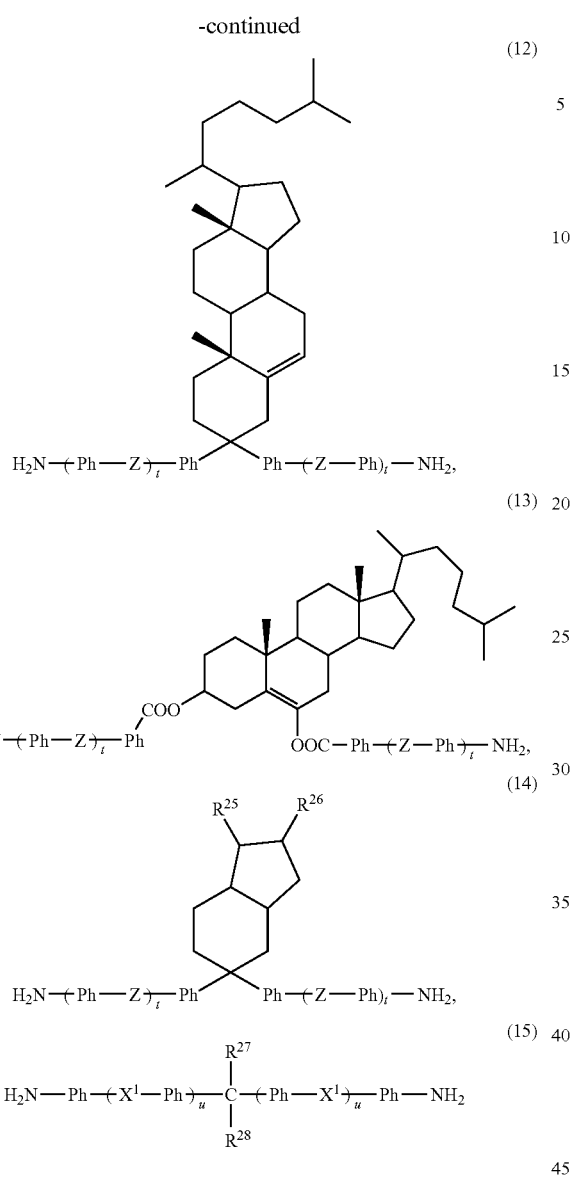

In formulas (11) to (14), $R^{24}$, $R^{25}$, and $R^{26}$ are independently hydrogen or a linear or branched alkyl group having 1 to 12 carbon atoms, Y is methylene, ring A represents a benzene or a cyclohexane ring, Z represents a single bond, $CH_2$, $CH_2CH_2$, or oxygen, r is an integer of 0 to 3, s is an integer of 0 to 5, t is an integer of 0 to 3, provided that when t is 2 or 3, each Z may be the same or different. In formula (15), $X^1$ represents a single bond, $CH_2$, $CH_2CH_2$, or oxygen, $R^{27}$ and $R^{28}$ are independently hydrogen, or an alkyl or perfluoroalkyl group having a linear or branched alkyl of 1 to 12 carbon atoms, but at least one of $R^{27}$ and $R^{28}$ is an alkyl or perfluoroalkyl group having a linear or branched alkyl of 3 or more carbon atoms, and u is an integer of 0 to 3, provided that when u is 2 or 3, each $X^1$ may be the same or different. Although this patent can solve a problem of image sticking and can adjust a pre-tilt angle arbitrarily, the pre-tilt angle merely ranges from 2.7 to 8.9 degree (see Tables 3 and 4 of the patent). In addition, the issue of orienting property of the liquid crystal is not addressed in this patent.

Therefore, there is a need in the art to provide a crystal orienting film that provides a greater range of pre-tilt angles and improved orienting property (i.e., no occurrence of undesired domains).

SUMMARY OF THE INVENTION

Therefore, the object of the present invention is to provide a diamine and a polyamic acid derived from the diamine, that can overcome the above drawbacks associated with the prior art.

According to one aspect of this invention, a diamine includes a structure of formula (I)

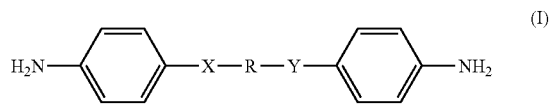

wherein X and Y are independently a divalence group selected from the group consisting of: —O—, —(C=O)—O—, —O—(C=O)—, —(C=O)—NH—, and —NH—(C=O)—; and R has a structure of formula (II):

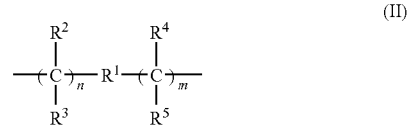

wherein $R^1$ is selected from the group consisting of:

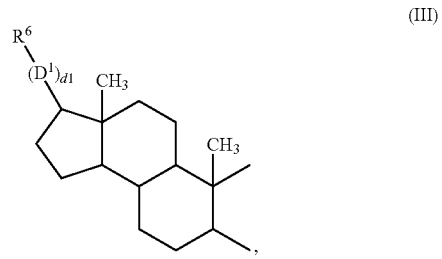

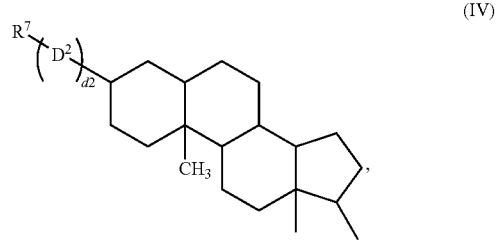

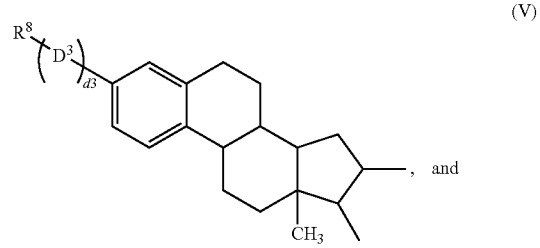

-continued

(VI)

wherein $D^1$, $D^2$, and $D^3$ are independently selected from the group consisting of: —NH—, —O—, and —S—; d1, d2, and d3 are independently 0 or 1; $R^6$, $R^7$, and $R^8$ are independently selected from the group consisting of: hydrogen, halogen, and $C_1$-$C_{30}$ alkyl; and Z is selected from the group consisting of:

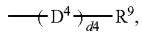
(VI-1)

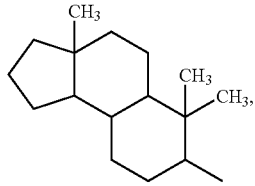
(VI-2)

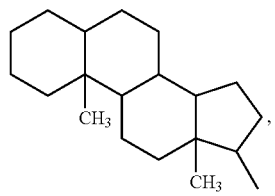
(VI-3)

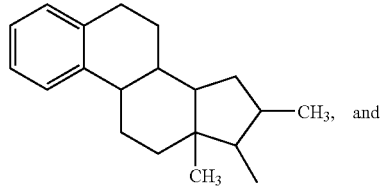
(VI-4)

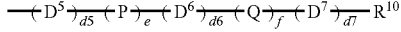
(VI-5)

wherein, in formulas (VI-1) and (VI-5), $D^4$, $D^5$, $D^6$, and $D^7$ are independently selected from the group consisting of:

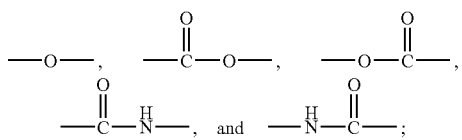

d4, d5, d6, and d7 are independently 0 or 1; $R^9$ is a linear chain alkyl; $R^{10}$ is selected from the group consisting of: hydrogen, fluorine, and $C_{1-6}$ alkyl; P and Q are independently selected from the group consisting of: 1,4-phenylene, 1,4-cyclohexylene, 1,4-cyclohexenylene, and 1,4-cyclohexadienylene; and e and f are independently an integer of 0 to 2, and cannot be 0 at the same time; and wherein, in formula (II), $R^2$, $R^3$, $R^4$, and $R^5$ are independently selected from the group consisting of: hydrogen and $C_1$-$C_3$ alkyl; and n and m are independently an integer of 0 to 3.

According to another aspect of this invention, a polyamic acid is prepared by reacting a diamine reactant with a tetracarboxylic dianhydride reactant. The diamine reactant contains a first diamine having a structure of formula (I)

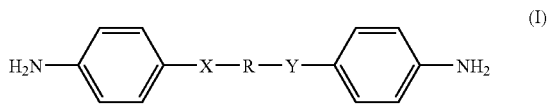
(I)

wherein X and Y are independently a divalence group selected from the group consisting of: —O—, —(C=O)—O—, —O—(C=O)—, —(C=O)—NH—, and —NH—(C=O)—; and R has a structure of formula (II):

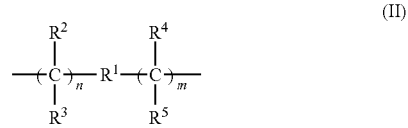
(II)

wherein $R^1$ is selected from the group consisting of:

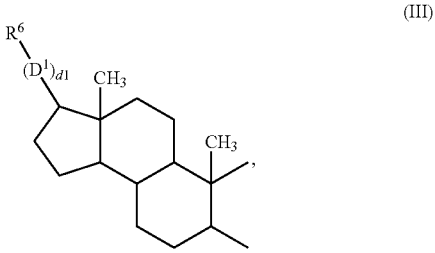
(III)

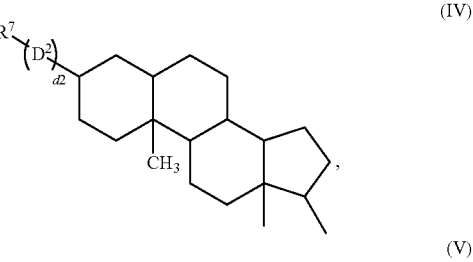
(IV)

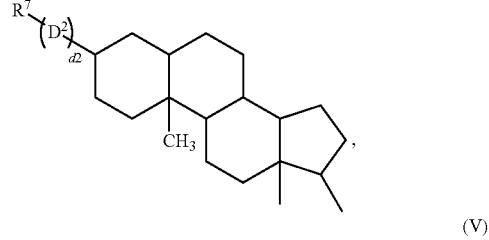
(V)

(VI)

wherein $D^1$, $D^2$, and $D^3$ are independently selected from the group consisting of: —NH—, —O—, and —S—; d1, d2, and d3 are independently 0 or 1; $R^6$, $R^7$, and $R^8$ are independently selected from the group consisting of: hydrogen, halogen, and $C_1$-$C_{30}$ alkyl; and Z is selected from the group consisting of:

$-(-D^4-)_{d4}-R^9,$ (VI-1)

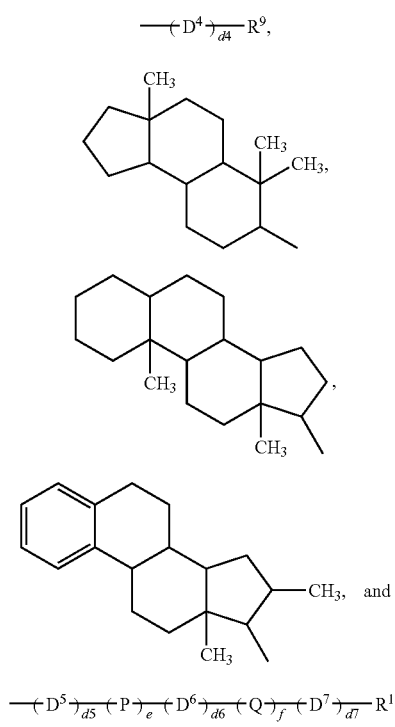

(VI-2)

(VI-3)

(VI-4)

$-(-D^5-)_{d5}-(-P-)_e-(-D^6-)_{d6}-(-Q-)_f-(-D^7-)_{d7}-R^{10}$ (VI-5)

wherein, in formulas (VI-1) and (VI-5), $D^4$, $D^5$, $D^6$, and $D^7$ are independently selected from the group consisting of:

$-O-$, $-\overset{O}{\underset{\|}{C}}-O-$, $-O-\overset{O}{\underset{\|}{C}}-$, $-\overset{O}{\underset{\|}{C}}-\overset{H}{\underset{|}{N}}-$, and $-\overset{H}{\underset{|}{N}}-\overset{O}{\underset{\|}{C}}-$;

d4, d5, d6, and d7 are independently 0 or 1; $R^9$ is a linear chain alkyl; $R^{10}$ is selected from the group consisting of: hydrogen, fluorine, and $C_{1-6}$ alkyl; P and Q are independently selected from the group consisting of: 1,4-phenylene, 1,4-cyclohexylene, 1,4-cyclohexenylene, and 1,4-cyclohexadienylene; and e and f are independently an integer of 0 to 2, and cannot be 0 at the same time; and wherein, in formula (II), $R^2$, $R^3$, $R^4$, and $R^5$ are independently selected from the group consisting of: hydrogen and $C_1$-$C_3$ alkyl; and n and m are independently an integer of 0 to 3.

DETAILED DESCRIPTION OF THE PREFERRED EMBODIMENTS

A diamine according to the present invention is shown to include a structure of formula (I)

$H_2N-\langle\text{phenyl}\rangle-X-R-Y-\langle\text{phenyl}\rangle-NH_2$ (I)

wherein X and Y are independently a divalence group selected from the group consisting of: $-O-$, $-(C=O)-O-$, $-O-(C=O)-$, $-(C=O)-NH-$, and $-NH-(C=O)-$; and R has a structure of formula (II):

$-(-\overset{R^2}{\underset{R^3}{C}}-)_n-R^1-(-\overset{R^4}{\underset{R^5}{C}}-)_m-$ (II)

wherein $R^1$ is selected from the group consisting of:

(III)

(IV)

(V)

$\underset{/}{\overset{\backslash}{\phantom{/}}}CH-Z,$ (VI)

wherein $D^1$, $D^2$, and $D^3$ are independently selected from the group consisting of: $-NH-$, $-O-$, and $-S-$; d1, d2, and d3 are independently 0 or 1; $R^6$, $R^7$, and $R^8$ are independently selected from the group consisting of: hydrogen, halogen, and $C_1$-$C_{30}$ alkyl; and Z is selected from the group consisting of:

$-(-D^4-)_{d4}-R^9,$ (VI-1)

-continued

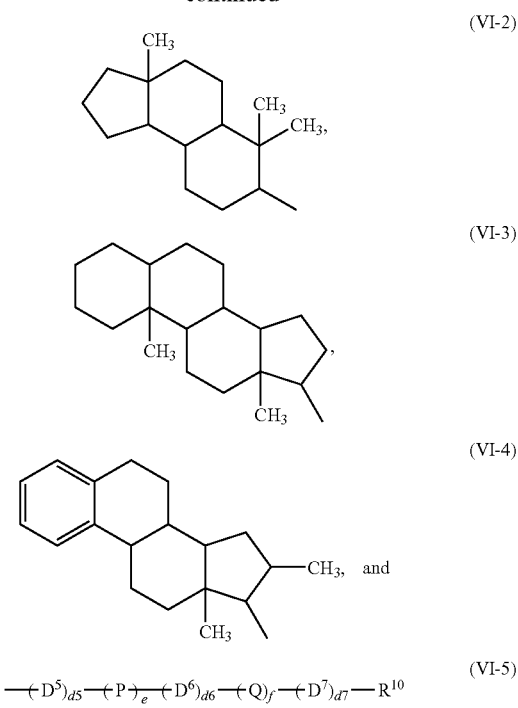

wherein, in formulas (VI-1) and (VI-5), $D^4$, $D^5$, $D^6$, and $D^7$ are independently selected from the group consisting of:

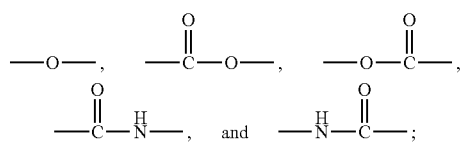

d4, d5, d6, and d7 are independently 0 or 1; $R^9$ is a linear chain alkyl; $R^{10}$ is selected from the group consisting of: hydrogen, fluorine, and $C_{1-6}$ alkyl; P and Q are independently selected from the group consisting of: 1,4-phenylene, 1,4-cyclohexylene, 1,4-cyclohexenylene, and 1,4-cyclohexadienylene; and e and f are independently an integer of 0 to 2, and cannot be 0 at the same time; and wherein, in formula (II), $R^2$, $R^3$, $R^4$, and $R^5$ are independently selected from the group consisting of: hydrogen and $C_1$-$C_3$ alkyl; and n and m are independently an integer of 0 to 3.

Preferably, each of X and Y of formula (I) is —O—.

Preferably, in formula (II), when $R^1$ is formula (III) $R^6$ is hydrogen or a $C_1$-$C_{15}$ alkyl, more preferably, a $C_1$-$C_{10}$ alkyl. In an example of this invention, $R^6$ is 2,6-dimethylhexyl.

Preferably, when $R^1$ is formula (IV), $R^7$ is hydrogen or a $C_1$-$C_{15}$ alkyl, more preferably, is hydrogen or a $C_1$-$C_{10}$ alkyl. In an example of this invention, $R^7$ is hydrogen.

Preferably, when $R^1$ is formula (V), $R^8$ is a $C_1$-$C_{15}$ alkyl, more preferably, a $C_1$-$C_{10}$ alkyl. In an example of this invention, $R^8$ is methyl.

Preferably, when $R^1$ is formula (VI), Z is formula (VI-1) Preferably, $R^9$ of formula (VI-1) is a $C_{11}$-$C_{30}$ alkyl having a linear chain, more preferably, a $C_{11}$-$C_{20}$ alkyl having a linear chain.

Preferably, Z of the formula (VI) is formula (VI-2).
Preferably, Z of the formula (VI) is formula (VI-3).
Preferably, Z of the formula (VI) is formula (VI-4).
Preferably, Z of the formula (VI) is formula (VI-5). Preferably, in formula (VI-5), each of $D^5$, $D^6$, and $D^7$ is —O—, and P and Q are independently 1,4-phenylene or 1,4-cyclohexylene. In an example of this invention, d5, d6, and d7 are 0; e and f are 1; P is 1,4-phenylene; Q is 1,4-cyclohexylene; and $R^1$ is pentyl. In another example of this invention, d5 is 0; d6 and d7 are 1; $D^6$ and $D^7$ are —O—; e and f are 1; P is 1,4-phenylene; Q is 1,4-cyclohexylene; and $R^{10}$ is pentyl.

Preferably, R of formula (I) is selected from the group consisting of:

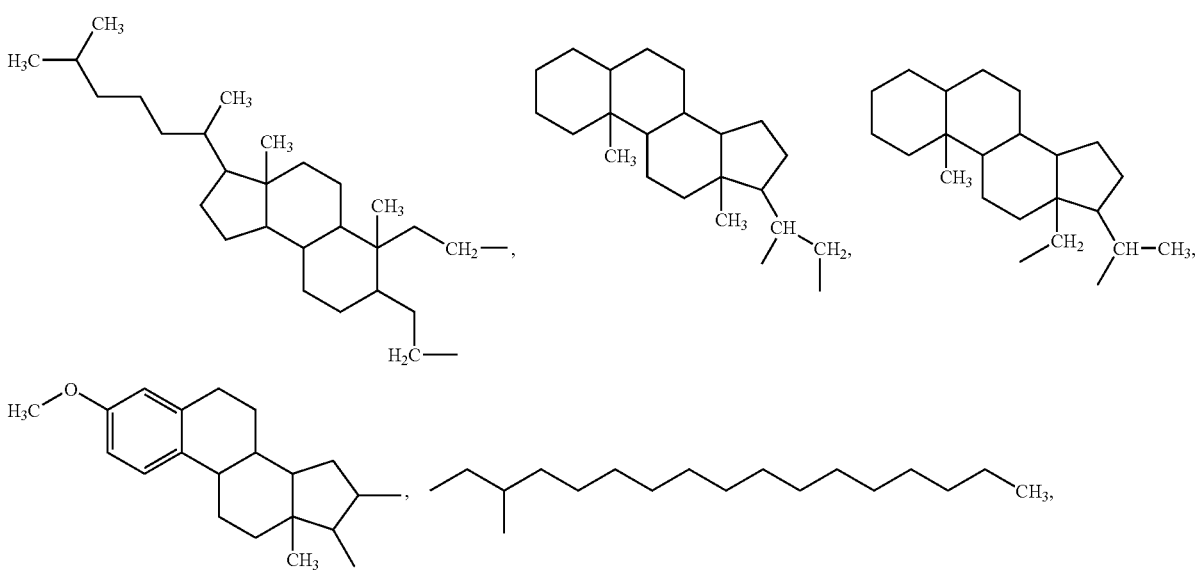

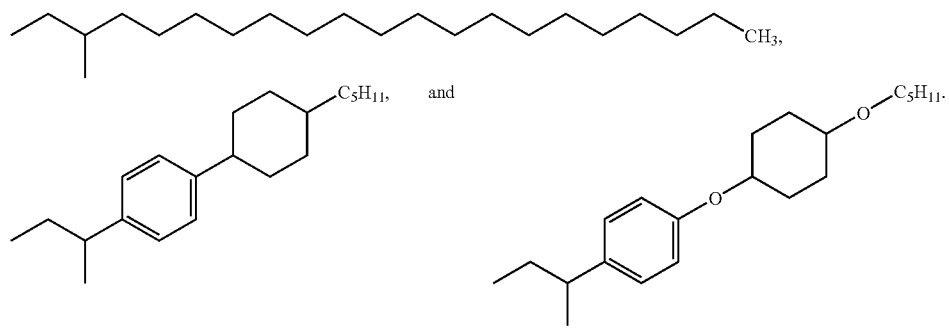

The diamine of this invention is prepared by undergoing a substitution reaction of an acid or alcohol with nitrobenzene (e.g., 4-chloro-nitrobenzene) having a good leaving group (e.g., halogen) followed by a reduction reaction. For example, formula (i) and/or formula (ii) are/is reacted with formula (iii), followed by selectively undergoing a reduction reaction.

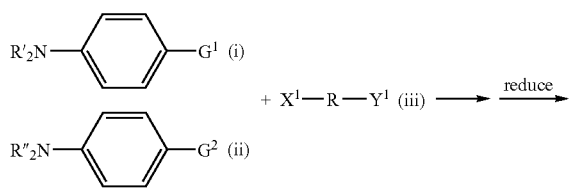

In formulas (i) and (ii), R' and R" are independently hydrogen or oxygen, and $G^1$ and $G^2$ are independently selected from the group consisting of: carboxyl, halogen, hydroxyl, and amino group. In formula (iii), $X^1$ and $Y^1$ are independently selected from the group consisting of: carboxyl, halogen, hydroxyl, and amino group, and R has a structure as defined above. When R' and R" are hydrogen, the reduction reaction can be dispensed with. When at least one of R' and R" is oxygen, the reduction reaction is required so as to obtain the diamine of formula (I).

A polyamic acid is also provided in this invention and is obtained by reacting a diamine reactant with a tetracarboxylic dianhydride reactant. The diamine reactant contains a first diamine having the structure of formula (I) as defined above.

The tetracarboxylic dianhydride reactant includes a tetracarboxylic dianhydride which is preferably selected from the group consisting of: pyromellitic dianhydride (PMDA), bicyclo(2,2,2)oct-7-ene-2,3,5,6-tetracarboxylic dianhydride (BCDA), 1,2,3,4-butanetetracarboxylic dianhydride (BDA), 2,3,5-tricarboxycyclopentylacetic dianhydride, 1,2,3,4-cyclobutanetetracarboxylic dianhydride, 1,3-dimethyl-1,2,3,4-cyclobutanetetracarboxylic dianhydride, 1,2,3,4-cyclopentanetetracarboxylic dianhydride, 1,2,3,4-tetramethyl-1,2,3,4-cyclobutanetetracarboxylic dianhydride, 1,3-diethyl-1,2,3,4-cyclobutanetetracarboxylic dianhydride, 1,2,3,4-tetraethyl-1,2,3,4-cyclobutanetetracarboxylic dianhydride, 1,2,3,4-tetrachloro-1,2,3,4-cyclobutanetetracarboxylic dianhydride, 1,2,3,4-tetrafluoro-1,2,3,4-cyclobutanetetracarboxylic dianhydride, and combinations thereof. In an example of this invention, the tetracarboxylic dianhydride is pyromellitic dianhydride.

Preferably, the diamine reactant further contains a second diamine selected from the group consisting of:
2,2-bis[4-(4-aminophenoxy)phenyl]propane (BAPP),
4,4'-diaminodicyclohexylmethane,
4,4'-bis(4-aminophenoxy)biphenyl (BAPB),
p-phenylenediamine, m-phenylenediamine,
4,4'-diamino-3,3'-dicarboxydiphenylmethane,
1,4-bis(4-aminophenyl)benzene, 4,4'-diaminobiphenyl,
3,3'-dimethyl-4,4'-diaminobiphenyl,
3,3'-dimethoxy-4,4'-diaminobiphenyl,
3,3'-dihydroxy-4,4'-diaminobiphenyl,
3,3'-dichloro-4,4'-diaminobiphenyl,
3,3'-dicarboxy-4,4'-diaminobiphenyl,
diaminodiphenylmethane, diaminodiphenyl ether,
2,2-diaminodiphenylpropane,
4,4'-diaminodiphenylsulfone,
1,3-bis(4-aminophenoxy)benzene,
1,4-bis(4-aminophenoxy)benzene,
4,4'-di(4-aminophenoxy)diphenylsulfone,
2,2-bis[4-(4-aminophenoxy)phenyl]propane,
2,2-bis[4-(4-aminophenoxy)phenyl]hexafluoropropane (HFBAPP), 2,2-bis(4-aminophenyl)hexafluoropropane,
2,2'-bis[4-(4-amino-2-trifluoromethylphenoxy)phenyl] hexafluoropropane,
4,4'-diamino-2,2'-bis(trifluoromethyl)biphenyl,
4,4'-bis[(4-amino-2-trifluoromethyl)phenoxy]octafluorobiphenyl, and combinations thereof. In an example of this invention, the second diamine is 2,2-bis[4-(4-aminophenoxy)phenyl]propane. It should be noted that the ratio of the first diamine to the second diamine in the diamine reactant can vary based on actual requirements.

Preferably, the molar ratio of the diamine reactant to the tetracarboxylic dianhydride reactant ranges from 1:1 to 1:0.9, more preferably, the molar ratio is 1:1.

A polyimide is also provided by undergoing dehydration and ring-closing reactions of the aforesaid polyamic acid. Specifically, a polyimide layer (i.e., a liquid crystal orienting film) is obtained by coating the aforesaid polyamic acid on a substrate followed by undergoing prebaking and post-baking processes to convert the polyamic acid to a ployimide.

EXAMPLES

Preparation of Diamines 0.1 mole of each of compounds of formulas (iv) listed in Table 1 was mixed with 0.22 mole pyridine, followed by dissolving the mixture in 50 g toluene and adding 0.22 mole 4-chloro-nitrobenzene therein so as to form a reaction solution. This reaction solution was subjected to reaction at 25° C.

for 6 hours. The reaction solution was then mixed with 100 ml pure water, followed by undergoing purification and concentration so as to obtain a solid product. The solid product was crystallized using methanol so as to form a powdery compound represented by formula (v) in page 26.

Each of the powdery compounds (v) thus obtained was dissolved in 30 g toluene so as to form a solution. The temperature of the solution was kept at 5° C. 0.02 g of 10% palladium on carbon (Pd—C) as a catalyst was added into the solution and 4.8 g hydrazine was slowly and drop wisely added therein followed by reacting at 160° C. for 6 hours. The solution was then mixed with 100 ml pure water, followed by undergoing purification and concentration so as to form a solid product. The solid product was crystallized using methanol so as to form powdery diamines listed in Table 2.

The structure of the compound of formula (v) formed from the compound (E') of formula (iv) and the structure of diamine (E) were determined using a nuclear magnetic resonance spectrometer (Bruker Avance 600). The data are shown as follows:

The compound of formula (v): $H^1$-NMR (400 MHz, $CDCl_3$), δ (ppm): 8.21 (dd, 4H); 6.99 (dd, 4H); 4.80 (t, 1H); 4.23 (d, 2H); 1.85 (t, 2H),; 1.25 (t, 20H); 0.88 (d, 3H)

Diamine (E): $H^1$-NMR (400 MHz, $CDCl_3$), δ (ppm): 6.78 (dd, 4H); 6.61 (dd, 4H); 4.34 (t, 1H); 3.99 (d, 2H); 1.76 (t, 2H); 1.27 (t, 20H); 0.89 (d, 3H)

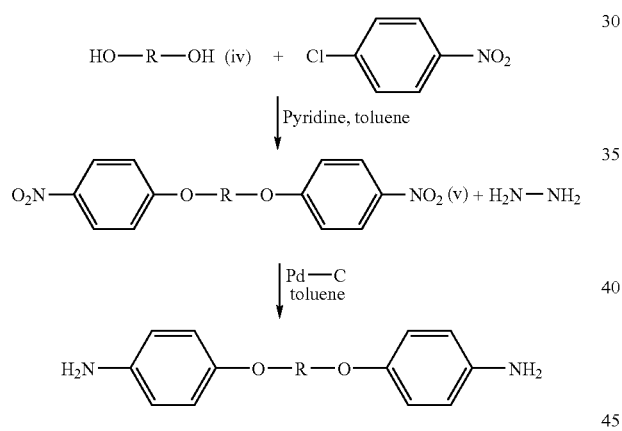

TABLE 1

| Compounds of formula (iv) | |
|---|---|
| 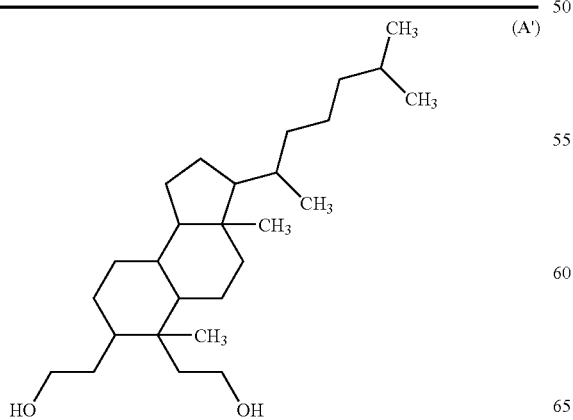 | (A') |
| 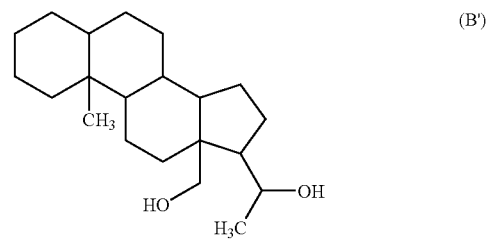 | (B') |
| 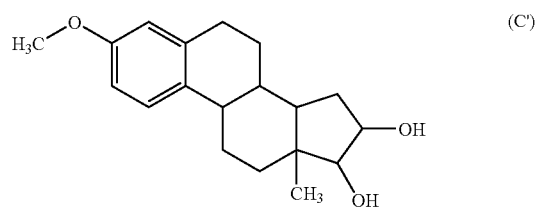 | (C') |
| 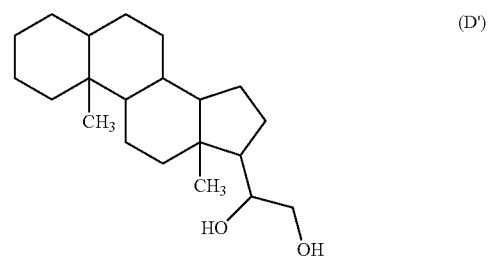 | (D') |
| 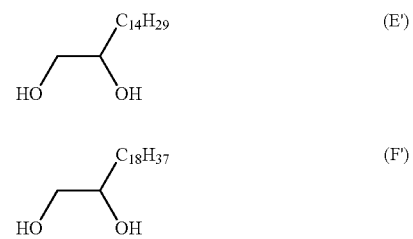 | (E') |
| | (F') |
| 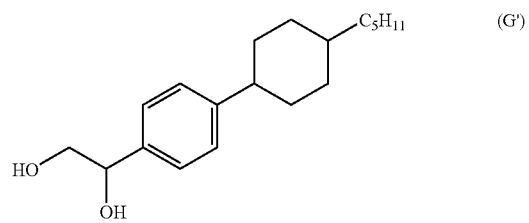 | (G') |
| 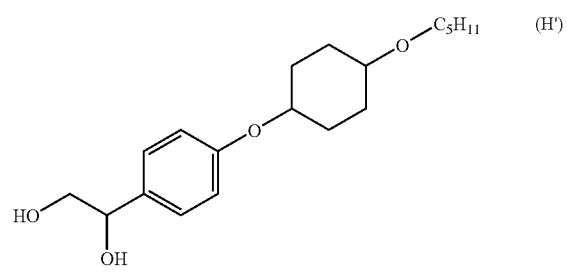 | (H') |

TABLE 2

| Diamine of formula (I) | |
|---|---|
| (A) | 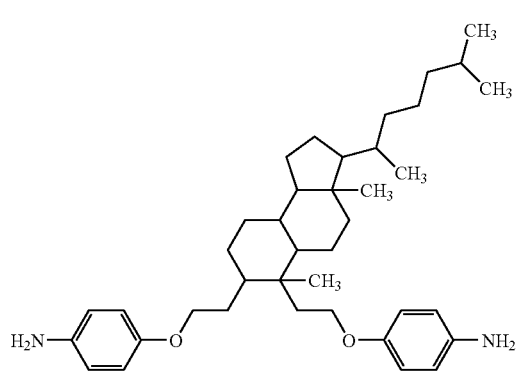 |
| (B) | 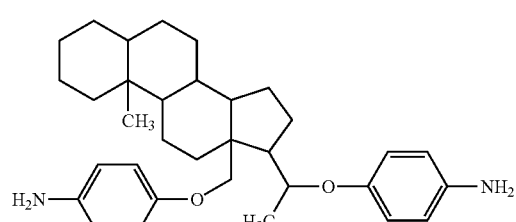 |
| (C) | 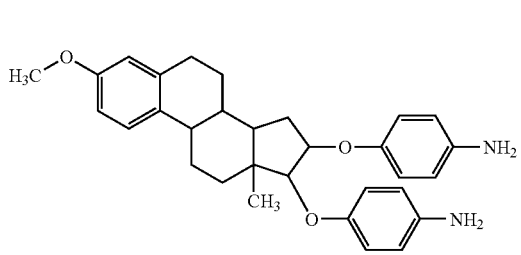 |
| (D) | 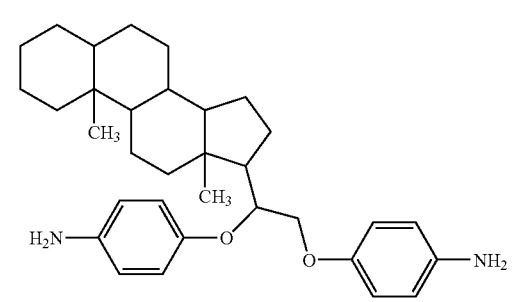 |
| (E) | 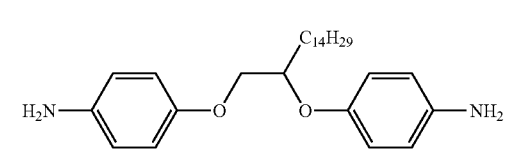 |
| (F) | 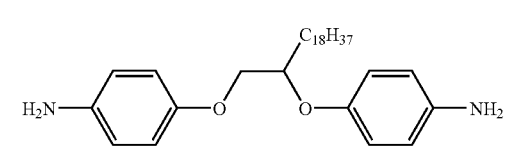 |
| (G) |  |

TABLE 2-continued

| Diamine of formula (I) | |
|---|---|
| (H) | 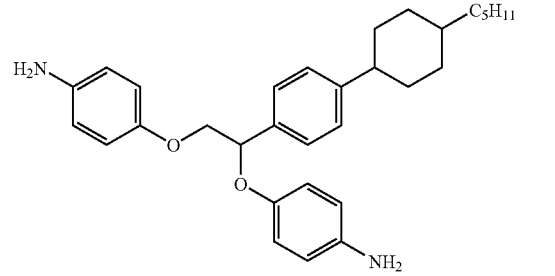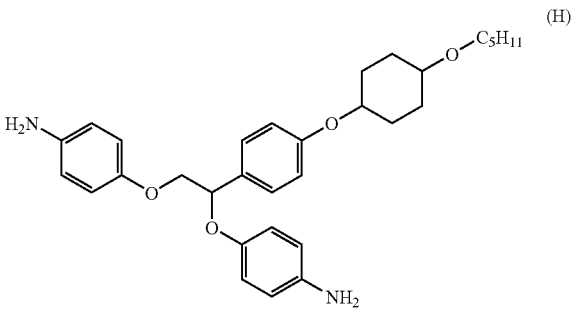 |

Preparation of Polyamic Acids

A diamine reactant containing diamine (A) or (E) and 2,2-bis[4-(4-aminophenoxy)phenyl]propane (BAPP) at different ratios listed in Table 3 was mixed with pyromellitic dianhydride (PMDA) at a molar ratio of 1:1, followed by adding 1 mmole of N-methyl-2-pyrrolidinone (NMP) therein so as to form a solution. The solution was subjected to reaction at 20° C. for 24 hours under stirring. NMP and ethylene glycol monobutyl ether at a ratio of 3:2 were added into the reacted solution so as to form a polyamic acid (PAA) solution containing 8% solid content.

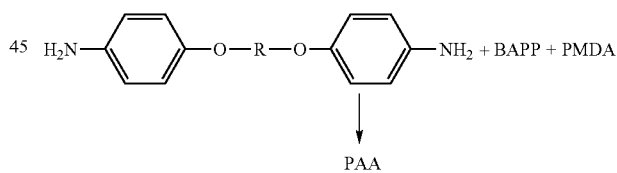

Preparation of Polyimide Layer (Liquid Crystal Orienting Film)

A polyimide layer was prepared by coating 3 g of each of the polyamic acid solutions thus obtained on a 50 mm×50 mm substrate of indium tin oxide (ITO) using a spin coater at a speed of 4000 rpm/20 sec, prebaking the substrate and the polyamic acid solution at 80° C. for 10 minutes, and post-baking the substrate and the polyamic acid at 250° C. for 60 minutes to convert polyamic acid into polyimide.

Preparation of Samples of Examples 1 to 9 and Comparative Example for Pre-Tilt Angle and Orienting Property Tests Two ITO substrates independently coated with the same polyimide layer (i.e., liquid crystal orienting film) thus formed were subjected to a rubbing process using a rubbing machine (ESR-1, available from E-SUN Precision Industrial Co., Ltd., pile impression: 0.5 mm, rubbing roller diameter: 170 mm (700 rpm), stage speed 100 mm/min, and the rubbing cloth used was YA-18). One of the ITO substrates coated with the orienting film was stacked in the following order with a first polyethylene terephthalate film (having a size of 50 mm in length, 5 mm in width, and 50 μm in thickness), a second polyethylene terephthalate film, and the other ITO substrate coated with the orienting film so as to form a laminate. The two orienting films on the ITO substrates of the laminate were arranged in such a manner to face the first and second polyethylene terephthalate films, respectively. Then, a liquid crystal (DN-132131, available from Daily Polymer Corp., having a phase transition temperature of 90° C., and free of a dopant) was filled into a space between the first and second polyethylene terephthalate films. The laminate filled with the liquid crystal was applied with an adhesive (an epoxy resin AB glue available from Nan-Ya Plastics Co. was used in these examples) on a periphery thereof, followed by heating the same at 90° C. for 5 minutes so as to obtain a testing sample. In the comparative example, the diamine reactant contained solely BAPP.

Test for Pre-Tilt Angle

The pre-tilt angle of the testing sample was determined using a tilt bias angle measuring system (TBA 107™, available from Autronic Co., Germany). It should be noted that the desired pre-tilt angle will be different for different liquid crystal materials. According to the liquid crystal material used in this invention, the pre-tilt angle is more preferably greater than 3°, and most preferably is 90°. The results are shown in Table 3.

Observation of Orienting Property

Undesired domains that occurred at the interface between the liquid crystal layer and the seal layer in the sample were observed using a polarizing microscope (Type 120, available from Nikon Company). The results are shown in Table 3. No undesired domain represents the best orienting property.

TABLE 3

| Examples | Diamine reactant | | | | Pre-tilt angle | Occurrence of the undesired domains |
| | Diamine (A) (mol %) | Diamine (E) (mol %) | BAPP (mol %) | dianhydride PMDA (mol %) | | |
| --- | --- | --- | --- | --- | --- | --- |
| 1 | — | 100 | — | 100 | 90.0 | Yes (very few) |
| 2 | — | 50 | 50 | 100 | 17.0 | No |
| 3 | — | 20 | 80 | 100 | 8.0 | No |
| 4 | — | 10 | 90 | 100 | 3.2 | No |
| 5 | — | 5 | 95 | 100 | 2.4 | No |
| 6 | 5 | — | 95 | 100 | 5.0 | No |
| 7 | 10 | — | 90 | 100 | 12.0 | No |
| 8 | 20 | — | 80 | 100 | 17.0 | No |
| 9 | 100 | — | — | 100 | 90.0 | Yes |
| Comparative example | — | — | 100 | 100 | 1.5 | No |

As shown in Table 3, the pre-tilt angle in each of Examples 1 to 9 is greater than that in the comparative example, and the pre-tilt angle in each of Examples 1 to 9 is increased with the increase of the content of diamine (A) or diamine (E). In addition, in examples 2 to 8 of this invention, undesired domains do not occur so that the orienting property of the liquid crystal can be improved.

In examples 1 and 9, the orienting property is not good because surface tension of the polyimide layer is decreased. The reason is that when the surface tension is decreased to a certain degree, the surface of the polyimide layer is difficult to be wetted by the liquid crystal, which results in an adverse effect on the orienting property. This problem can be compensated by changing the liquid crystal material or adjusting the content ratio of diamine (A) and/or (E).

With the novel diamine, the polyimide layer (the liquid crystal orienting film) of this invention can not only provide a desired pre-tilt angle but also improve orienting property for the liquid crystal.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

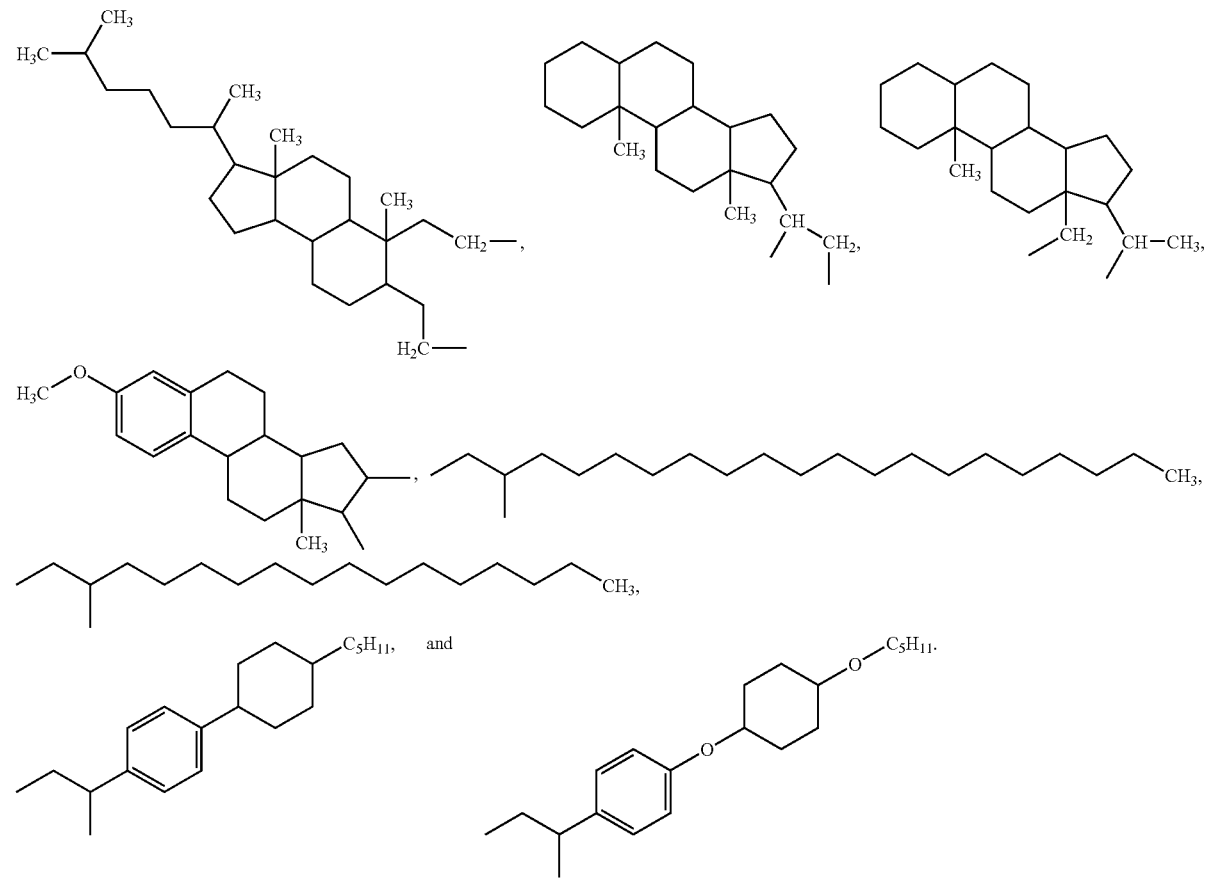

What is claimed is:

1. A diamine comprising a structure of formula (I)

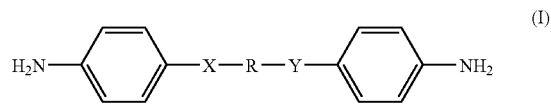

wherein X and Y are independently a divalence group selected from the group consisting of: —O—, —(C=O)—O—, —O—(C=O)—, —(C=O)—NH—, and —NH—(C=O)—; and R has a structure of formula (II):

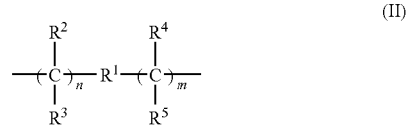

wherein $R^1$ is selected from the group consisting of:

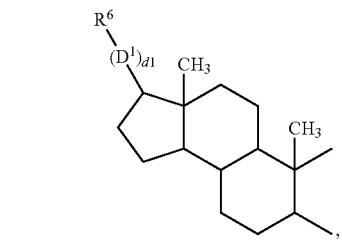
(III)

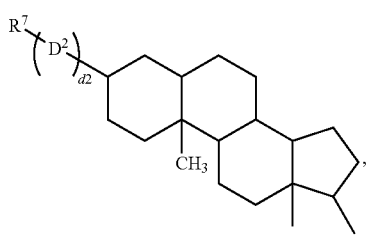
(IV)

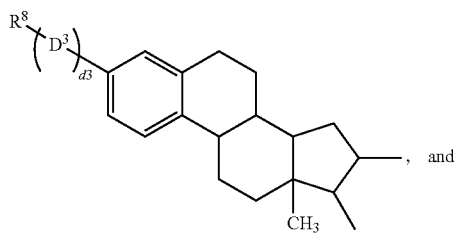
, and
(V)

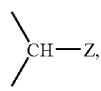
(VI)

wherein $D^1$, $D^2$, and $D^3$ are independently selected from the group consisting of: —NH—, —O—, and —S—; d1, d2, and d3 are independently 0 or 1; $R^6$, $R^7$, and $R^8$ are independently selected from the group consisting of: hydrogen, halogen, and $C_1$-$C_{30}$ alkyl; and Z is selected from the group consisting of:

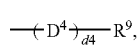
(VI-1)

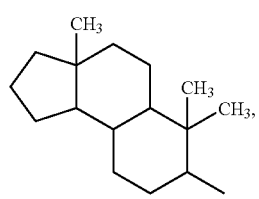
(VI-2)

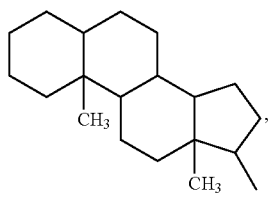
(VI-3)

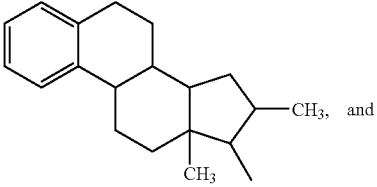
(VI-4)

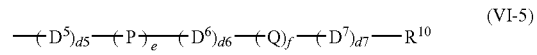
(VI-5)

wherein, in formulas (VI-1) and (VI-5), $D^4$, $D^5$, $D^6$, and $D^7$ are independently selected from the group consisting of:

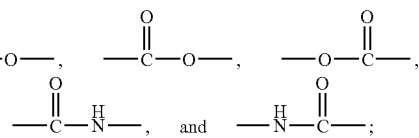

d4, d5, d6, and d7 are independently 0 or 1; $R^9$ is a $C_{11\text{-}30}$ linear chain alkyl; $R^{10}$ is selected from the group consisting of: hydrogen, fluorine, and $C_{1\text{-}6}$ alkyl; P and Q are independently selected from the group consisting of: 1,4-phenylene, 1,4-cyclohexylene, 1,4-cyclohexenylene, and 1,4-cyclohexadienylene; and e and f are independently an integer of 0 to 2, and cannot be 0 at the same time;

wherein, in formula (II), $R^2$, $R^3$, $R^4$, and $R^5$ are independently selected from the group consisting of: hydrogen and $C_1$-$C_3$ alkyl; and n and m are independently an integer of 0 to 3; and wherein, when $R^1$ is formula (VI) and Z is formula (VI-1), n and m cannot be 0 at the same time.

2. The diamine of claim 1, wherein each of X and Y of formula (I) is —O—.

3. The diamine of claim 2, wherein $R^6$ of formula (III), $R^7$ of formula (IV), and $R^8$ of formula (V) are independently selected from the group consisting of: hydrogen and $C_1$-$C_{15}$ alkyl.

4. The diamine of claim 1, wherein $R^1$ of formula (II) has the structure of formula (III), and wherein $R^6$ of formula (III) is $C_1$-$C_{10}$ alkyl.

5. The diamine of claim 1, wherein $R^1$ of formula (II) has the structure of formula (IV), and wherein $R^7$ of formula (IV) is hydrogen.

6. The diamine of claim 1, wherein $R^1$ of formula (II) has the structure of formula (V), and wherein $R^8$ of formula (V) is methyl.

7. The diamine of claim 1, wherein $R^1$ of formula (II) has the structure of formula (VI).

8. The diamine of claim 7, wherein Z of formula (VI) has the structure of formula (VI-1).

9. The diamine of claim 8, wherein $R^9$ of formula (VI-1) is a $C_{11\text{-}20}$ alkyl having a linear chain.

10. The diamine of claim 7, wherein Z of formula (VI) has the structure of formula (VI-2).

11. The diamine of claim 7, wherein Z of formula (VI) has the structure of formula (VI-3).

12. The diamine of claim 7, wherein Z of formula (VI) has the structure of formula (VI-4).

13. The diamine of claim 7, wherein Z of formula (VI) has the structure of formula (VI-5).

14. The diamine of claim 13, wherein each of $D^5$, $D^6$, and $D^7$ of formula (VI-5) is —O—.

15. The diamine of claim 13, wherein P and Q of formula (VI-5) are independently selected from the group consisting of: 1,4-phenylene and 1,4-cyclohexylene.

16. The diamine of claim 13, wherein d5, d6, and d7 are 0; e and f are 1; P is 1,4-phenylene; Q is 1,4-cyclohexylene; and $R^{10}$ is pentyl.

17. The diamine of claim 13, wherein d5 is 0; d6 and d7 are 1; $D^6$ and $D^7$ are —O—; e and f are 1; P is 1,4-phenylene; Q is 1,4-cyclohexylene; and $R^{10}$ is pentyl.

18. The diamine of claim 1, wherein R of formula (I) is selected from the group consisting of: